United States Patent [19]

Stengel et al.

[11] 4,084,346
[45] Apr. 18, 1978

[54] METHOD AND ARRANGEMENT FOR OPTIMALLY SUPPLYING AUTOTROPHIC ORGANISMS WITH $CO_2$ NUTRIENT

[75] Inventors: Eberhard Stengel, Dortmund; Carl Johannes Soeder, Dortmund-Brucherhof, both of Germany

[73] Assignee: Gesellschaft fur Strahlen- und Umweltforschung mbH, Munich, Germany

[21] Appl. No.: 749,893

[22] Filed: Dec. 13, 1976

[30] Foreign Application Priority Data

Dec. 13, 1975 Germany .............................. 2556290

[51] Int. Cl.$^2$ .............................................. A01G 7/00
[52] U.S. Cl. ................................................... 47/1.4
[58] Field of Search ...................... 47/1.4, 58; 210/10, 210/11, 15, 3

[56] References Cited

U.S. PATENT DOCUMENTS

| | | | |
|---|---|---|---|
| 2,658,310 | 11/1953 | Cook | 47/1.4 |
| 3,403,471 | 10/1968 | Clement | 47/1.4 |
| 3,462,360 | 8/1969 | McKinney | 47/1.4 X |
| 3,504,185 | 3/1970 | Zweig et al. | 47/1.4 X |
| 3,650,068 | 3/1972 | Meyer et al. | 47/1.4 |
| 3,768,200 | 10/1973 | Klock | 47/1.4 |
| 3,955,318 | 5/1976 | Hulls | 47/1.4 |

FOREIGN PATENT DOCUMENTS

| | | | |
|---|---|---|---|
| 2,145,787 | 9/1972 | Germany | 47/1.4 |
| 184,555 | 8/1966 | U.S.S.R. | 47/1.4 |
| 371,895 | 5/1973 | U.S.S.R. | 47/1.4 |

*Primary Examiner*—E. H. Eickholt
*Attorney, Agent, or Firm*—Spencer & Kaye

[57] ABSTRACT

A method is provided for optimally supplying autotrophic organisms with $CO_2$ nutrient, the requirement for the nutrient fluctuating in dependence on growth and thus on the incident light, temperature and the density of the organisms. The pH in a culture channel containing the organisms is continuously measured and the introduction of $CO_2$ into the culture channel is regulated in response to the measured pH. An arrangement is provided for practicing the method and comprises a channel in which a suspension of the organisms can be moved in one direction, at least one discharge means in the channel for introducing the $CO_2$ gas into suspension, at least one control member connected to the discharge means for controlling the operation of the discharge means, at least one pH measuring means in the channel for immersion into the suspension, and a circuit connecting the pH measuring means and the control member to actuate the control member for introducing the $CO_2$ in response to the pH measured by the pH measuring means.

6 Claims, 10 Drawing Figures

METHOD AND ARRANGEMENT FOR OPTIMALLY SUPPLYING AUTOTROPHIC ORGANISMS WITH $CO_2$ NUTRIENT

BACKGROUND OF THE INVENTION

The present invention relates to a method and arrangement for practising the method for the optimal supplying of autotrophic organisms with carbon dioxide nutrient, the nutrient requirement fluctuating in dependence on growth and thus on the incident light, temperature and the density of the organisms.

In all cultures of photoautotropic organisms, carbon dioxide must be supplied as the main nutrient. The carbon dioxide attaches itself to water and forms carbonic acid which then dissociates into hydrated $H^+$ ions and $HCO_3^-$ ions. Every introduction of $CO_2$ into aqueous systems in the slightly acid to alkali range, as, for example, nutrient solutions for algae, is thus connected with a reduction in pH. Conversely, every removal of $CO_2$ or $H_2CO_3$, respectively, or of $HCO_3^-$ leads to a rise in pH. The quantity of $CO_2$ required by the organisms at a certain point in time depends on a plurality of factors, mainly, light, temperature and density of the organisms. Under certain circumstances, in particular, under controlled out door conditions, the quantity of $CO_2$ required by the organisms is subject to considerable fluctuations.

There have been attempts to provide economically justifiable quantitites of $CO_2$ supplies which are always the most favorable under fluctuating conditions, but this has not been possible with conventional systems for introducing $CO_2$ into the cultures. These known systems are described, for example, in the summary report by the German Botanical Society, Volume 83, Issue No. 11 (1970), pages 589 to 606, and introduce the $CO_2$, which is important for the growth of the microorganisms, e.g., the algae, either intermittently by means of diffusion boxes or constantly and uniformly through bypass gas exchangers. The former system using intermittent $CO_2$ introduction, according to 1), has the advantage of good $CO_2$ utilization, but has the drawback that it requires much work to fill the system with $CO_2$, the upwardly closed diffusion boxes are difficult to clean, flow resistance is high and the yields per unit area or algae growth, respectively, are relatively poor due to insufficient $CO_2$ supply. On the other hand, any type of system using constant and uniform $CO_2$ introduction has the drawback that it will not be optimally adapted to the prevailing light conditions which principally fluctuate in the course of a day, so that over long periods of time there will exist a lack of $CO_2$ or an excess of $CO_2$.

1) H. Kraut and M. -E. Meffert, Forschungsber. Land Nordrhein-Westfalen, No. 1648, p. 12-13 (1966)

SUMMARY OF THE INVENTION

It is a primary object of the present invention to supply microorganisms growing in open channels with $CO_2$ fully automatically corresponding to the respective demands of the microorganisms, i.e., in direct dependence on the photosynthesis taking place under daylight, without malfunctions and with minimum attendance.

It is a further object of the present invention to supply algae in such a manner, and to have the $CO_2$ utilization and the ratio of $CO_2$ introduced to $CO_2$ absorbed by the algae as high as possible, with the amount of incident light being as high as possible, the flow resistance in the channel being relatively low, and directed regulation of the gas exchange being possible.

Another object of the present invention is to provide an apparatus or system for performing the method.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects, and in accordance with its purpose, the present invention, as embodied and broadly described, provides a method for optimally supplying autotrophic organisms with $CO_2$ nutrient, the requirement for the nutrient fluctuating in dependence on growth and thus on the incident light, temperature and the density of the organisms, comprising: continuously measuring the pH in a culture channel containing the organisms, and regulating the introduction of $CO_2$ into the culture channel in response to the measured pH.

In a preferred embodiment of the invention, the autotrophic organisms comprise algae organisms.

In another aspect, the present invention provides an arrangement for optimally supplying autotrophic organisms with $CO_2$ nutrient comprising: a channel in which a suspension of the organisms can be moved in one direction, at least one discharge means in the channel for introducing the $CO_2$ gas into the suspension, at least one control member connected to the discharge means for controlling the operation of the discharge means, at least one pH measuring means in the channel for immersion into the suspension, and a circuit connecting the pH measuring means and the control member to actuate the control member for introducing the $CO_2$ in response to the pH measured by the pH measuring means.

In order to better use the $CO_2$ gas charged into the channel, a preferred embodiment of the arrangement according to the present invention includes at least one barrier layer in the channel parallel to the direction of flow of the suspension above and downstream of the $CO_2$ discharge means, which barrier layer is light transmitting, but does not permit gas to penetrate. The barrier layer can advantageously be formed of foil or a plastic or glass plate, respectively, which is fastened below the surface of the suspension by means of at least one mount. The height of the foils or plates, respectively, with respect to the surface of the channel can be adjustable.

In another embodiment of the arrangement according to the present invention, the suspension is kept in motion by impeller wheels and the control members are formed by solenoid valves which are controlled by way of a relay in the circuit.

The method and system according to the present invention now makes it possible to always assure quantities which accurately correspond to the assimilatory $CO_2$ absorption by the organisms, differences in $CO_2$ lost to the atmosphere being likewise considered automatically. In the present invention, the introduction of $CO_2$, generally by means of pure one hundred percent carbon dioxide gas, is controlled via a pH-static control system. The $CO_2$ discharge means provided in the open culture channel preferably are followed by a barrier layer in the form of floating foils or fixed plastic or glass plates which float on the surface of the suspension or are immersed in the suspension to a greater or lesser degree as required, so that the CO₂ entering into the culture medium will not immediately rise to the surface of the water and thus be able to escape to the atmosphere to a significant degree, but is rather held below the barrier layer and thus forced to spend a significantly longer period of time in contact with the culture medium. The pH is consequently a value which does not significantly change due to further removal of nutrients other than $CO_2$, particularly when suitable sources of nitrogen are used as is the case with certain algae nutrient solutions, and is a value which is suitable as a parameter for the control of the $CO_2$ introduction.

It is to be understood that both the foregoing general description and the following detailed description are exemplary, but are not restrictive of the invention.

BRIEF DESCRIPTION OF THE DRAWINGS

The accompanying drawings, in which like numbers indicate like parts, illustrate examples of presently preferred embodiments of the invention and, together with the description, serve to explain the principles of the invention.

The present invention will now be described in detail with the aid of an embodiment which is illustrated in FIGS. 1 to 3 and with the aid of diagrams shown in FIGS. 4 to 10.

Of the drawings:

FIG. 1 is a longitudinal sectional view of an arrangement, including a channel, made in accordance with the teachings of the present invention for practicing the method of the present invention;

FIG. 2 is a cross sectional view of the channel of FIG. 1 taken along line 2—2;

FIG. 3 is a schematic representation of the control or regulating circuit for the arrangement of the present invention;

FIGS. 4 to 7 are diagrams which are more fully explained below; and

FIGS. 8 to 10 are curves which show various values measured on certain days during which the present invention was practiced.

DESCRIPTION OF PREFERRED EMBODIMENTS

Figure 1:
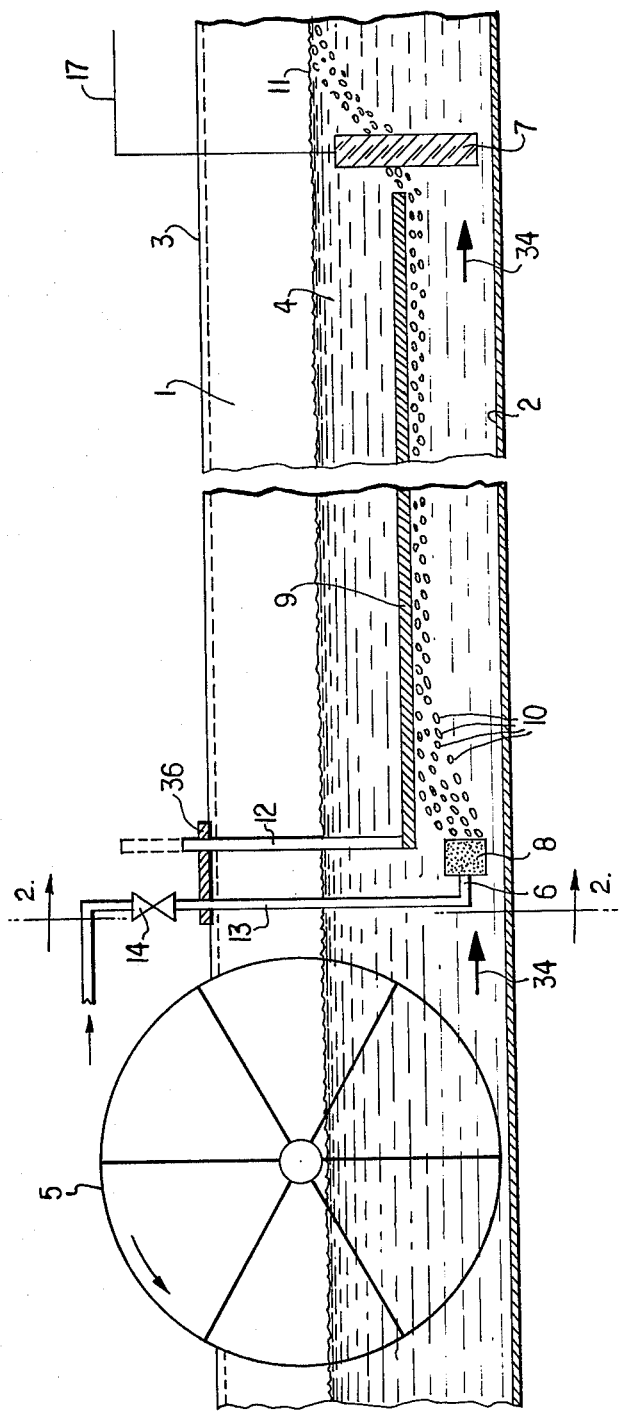
Figure 2:
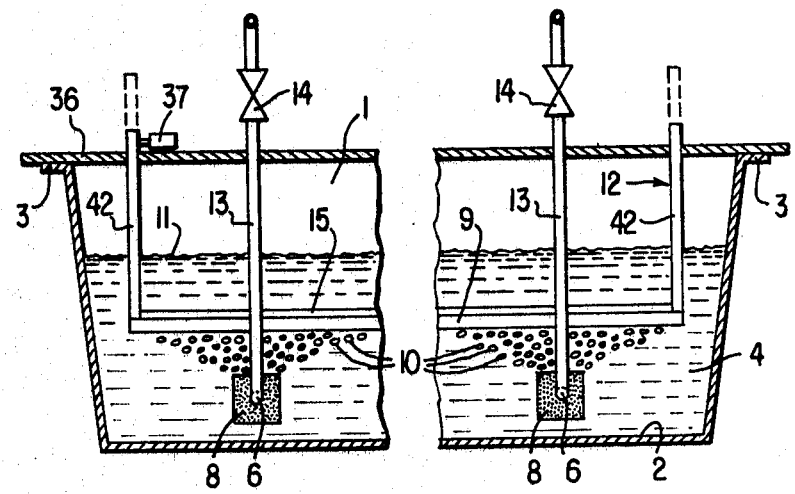

Referring to FIG. 1, there is shown a longitudinal sectional view of an open channel 1 of the type known as an oxidation ditch in the waste water treatment art, including a channel bottom 2 and an edge 3 of the channel. Within channel 1, an algae suspension 4 is continuously moved in the direction indicated by the arrows 34 by means of impeller wheels 5 which are shown schematically. $CO_2$ is introduced into suspension 4 in channel 1 through discharge means in the form of at least one outlet 6 which contains a distributor head 8 which introduces $CO_2$ gas bubbles 10 into suspension 4. When more than one $CO_2$ outlet is provided, they preferably are arranged at uniform intervals across the width of the channel in order to effect uniform distribution of the $CO_2$. As seen in FIG. 2, two outlets 6 and their distributor heads 8 are immersed in suspension 4 across the width of channel 1 in order to better utilize and control the introduction of $CO_2$. As seen in FIGS. 1 and 2, outlets 6 are connected to a $CO_2$ reservoir or a gasification system, not shown in detail, by means of lines 13 and solenoid valves 14. Solenoid valves 14, as explained below, serve as control members for controlling the introduction of $CO_2$ into outlets 6 and suspension 4. Surface diffusion or gas exchangers can also be provided for the purpose of introducing the $CO_2$ into channel 1.

Figure 3:
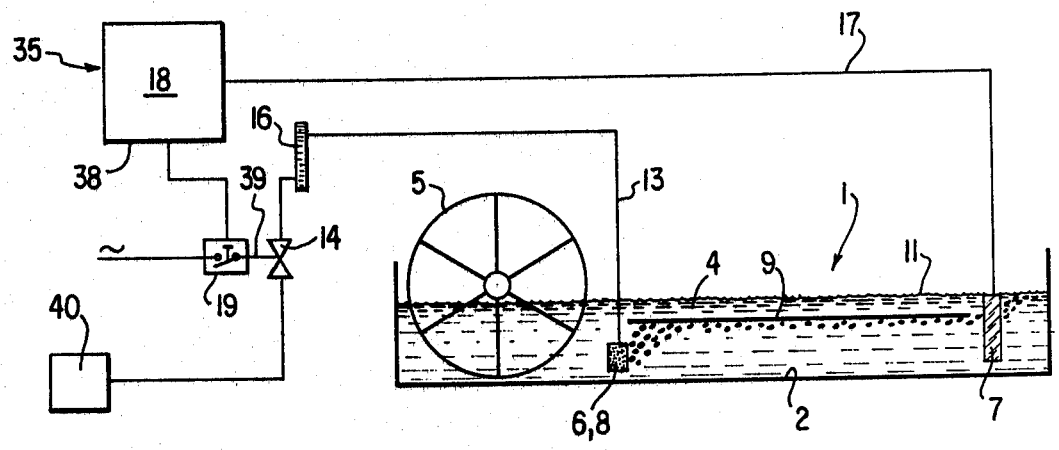

A pH measuring means in the form of a glass electrode 7, such as an Ingold Glass Electrode of the Type 405 T, is connected via an electrical connecting line 17 to a control circuit shown in FIG. 3 by the reference numeral 35 and described in greater detail hereafter.

In order to be able to better utilize the $CO_2$ gas streaming out of outlets 6, a barrier layer 9, in the form of foils or plastic or glass plates, respectively, is provided immediately above the outlets 6 for the $CO_2$ gas. By so positioning barrier layer 9, gas bubbles 10 are further transported through suspension 4 below barrier layer 9, before they are able to escape to the atmosphere at the surface 11 of suspension 4. A prerequisite for further transport of the gas bubbles 10 is that the suspension be moved continuously in one direction by means of impeller wheels 5.

Barrier layer 9 can be positioned below surface 11 of suspension 4 by fastening means, such as a mount. When barrier layer 9 is in the form of a light transmitting, but gas impermeable foil, only one mount 12 can be used on one side of foil 9 located at the end adjacent $CO_2$ outlet 6. The mount 12 or the foil 9, respectively, can be adjusted in height with respect to the level of channel edge 3 and surface 11 of suspension 4, as shown by the dotted lines in FIGS. 1 and 2. The foil is supported by suspension 4. The length of the foil panel may be ten meters or more. The width of barrier layer 9 can be between about 0.5 and about 4 meters.

FIG. 2 is a cross sectional view of channel 1 with algae suspension 4. The mount 12 is here comprised of two vertical bars 42 on opposite sides of foil 9 and which are connected together by means of a transverse bar 15, to which foil 9 is fastened. A transverse support rod 36 rests on opposite edges 3 of channel 1. A motor 37 is positioned on support rod 36 and is connected to vertical bar 12 by conventional means, such as gearing, to adjust the height of barrier layer 9 with respect to the level of channel edge 3 or surface 11 of suspension 4. When barrier layer 9 is in the form of a plastic or glass plate, a further mount corresponding to mount 12 is necessary at the other end of channel 1, when seen in the direction of flow of suspension 4, that is, at the end adjacent measuring electrode 7.

FIG. 3 is a schematic representation of the circuit 35 to control the pH in open channel 1 and comprises a pH regulator 18 and a relay 19 connected to each other by an electrical connecting line 38. The pH regulator 18 is a control amplifier with limit contacts and is connected to pH measuring electrode 7 by electrical connecting line 17. Relay 19 is connected to solenoid valve 14 by an electrical connecting line 39. As shown in FIG. 3, solenoid valve 14 is connected with a $CO_2$ reservoir 40, not shown in detail, and a flow meter 16 is in pipeline 13 between outlet 6 and solenoid valve 14. In operation, as soon as the pH within channel 1 or the algae suspension 4, respectively, has reached a certain adjustable upper value by way of assimilatory activity of the algae, relay 19 actuates solenoid valve 14 to open the inlet for the $CO_2$. $CO_2$ is now introduced into the algae suspension 4 until the subsequent reduction in pH by about 0.1 pH causes relay 19 to drop and solenoid valve 14 to close. This process is repeated as long as the algae assimilate (see, in this connection, the measuring diagrams of FIGS. 7 to 10, described in detail hereafter). The frequency of operation of solenoid valve 14 thus is set automatically in dependence on the consumption of $CO_2$ by the algae which, in turn, varies in consideration of, among other things, the amount of incident light (see also FIGS. 8 and 10 described in detail hereafter).

Figure 4:
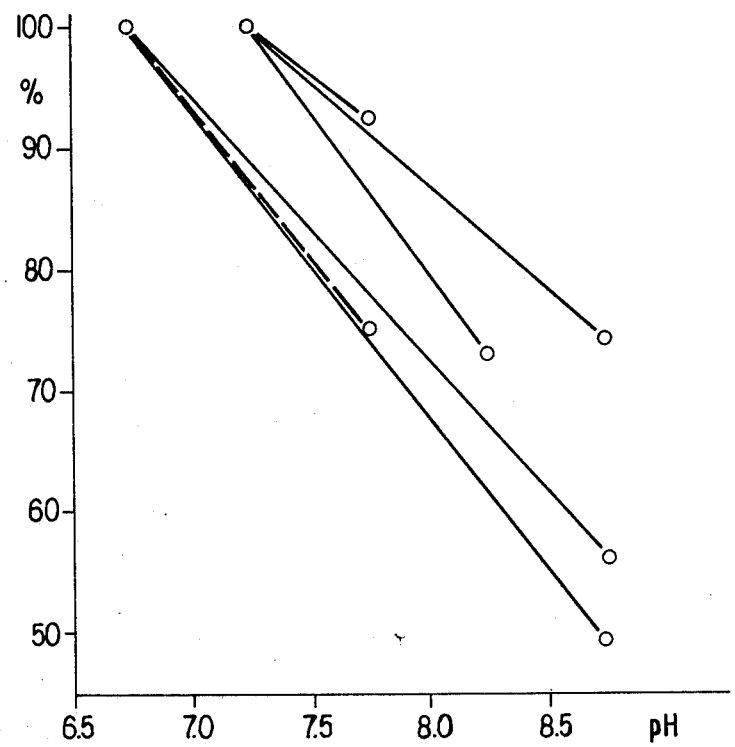

FIG. 4 shows in lines 20 to 24 the dependence of the growth of the algae on the pH in percent of the optimum growth rate for experiments conducted under out door conditions for Scenedesmus algae. Each line represents an experiment and the plotted values on each line were obtained by controlling the pH in accordance with the teachings of the present invention so that each plotted value is obtained at an essentially static pH. Line 25 shows a similar experiment with Coelastrum algae.

Figure 5:
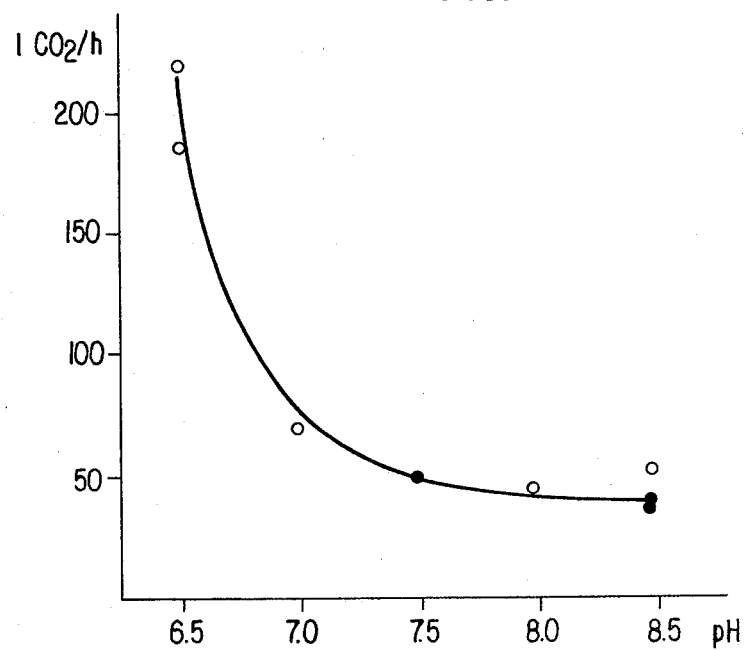

FIG. 5 shows a plot of the relationship between the $CO_2$ introduction in liters of carbon dioxide per hour and the pH for Scenedesmus cultures under out door conditions. The experiment was made in the summer of 1974 and was conducted in two basins, with the size of one basin being 81 m² and the size of the second basin being 76 m². The suspension volume in each basin was 12 m³. The measured values are average values from tests made under comparable growth and light conditions. The experiments were conducted in accordance with the present invention under pH static conditions. From FIG. 5 it follows e.g. that about four times as much $CO_2$ is needed to keep the suspension at pH 6.5 than required for maintaining pH 8.5.

Figure 6:
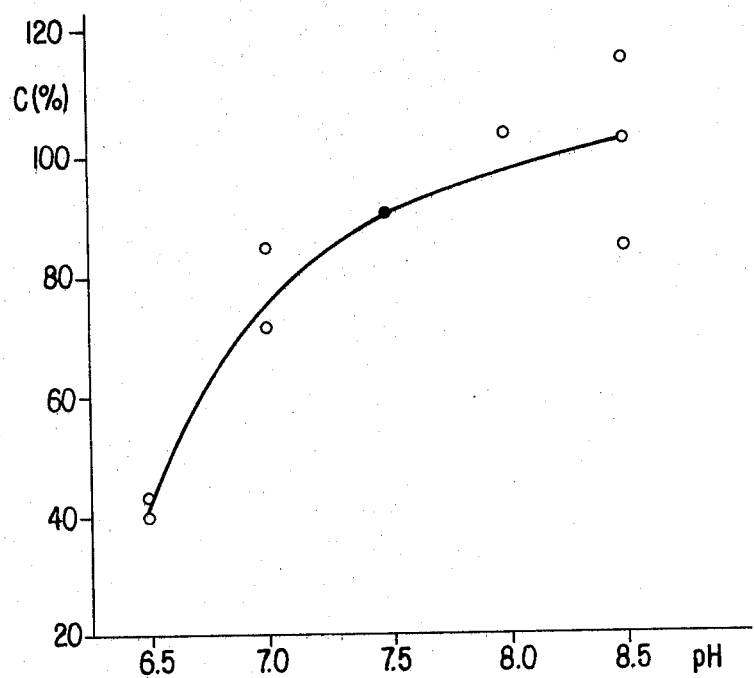

FIG. 6 shows the dependency of the carbon utilization efficiency in percent of the quantity introduced on the pH. Carbon utilization is here defined as "C incorporated", the C originating from the carbon dioxide which has been incorporated in the dry algae substance. The other conditions correspond to those of FIG. 5.

Figure 7:
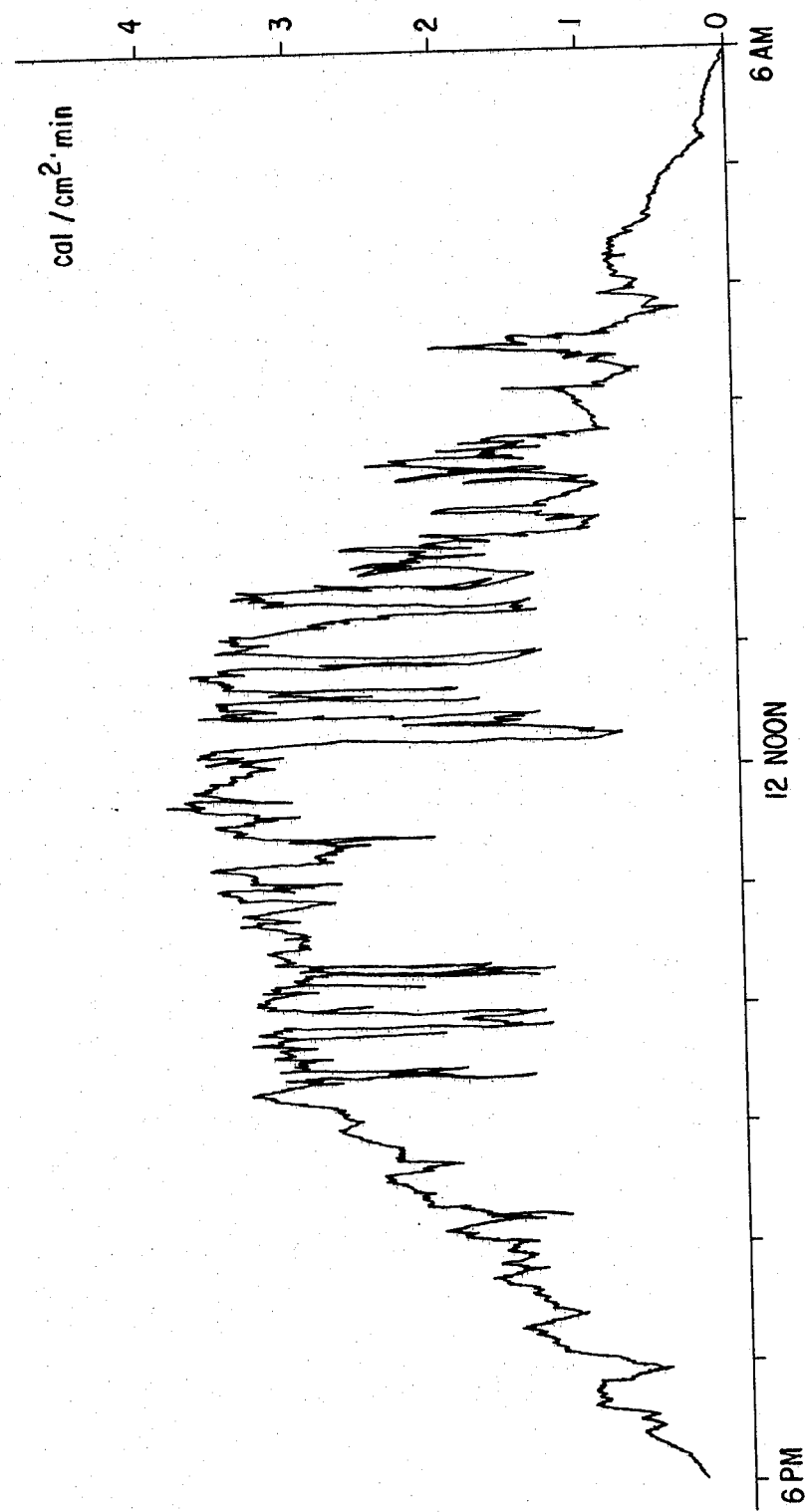
Figure 8:
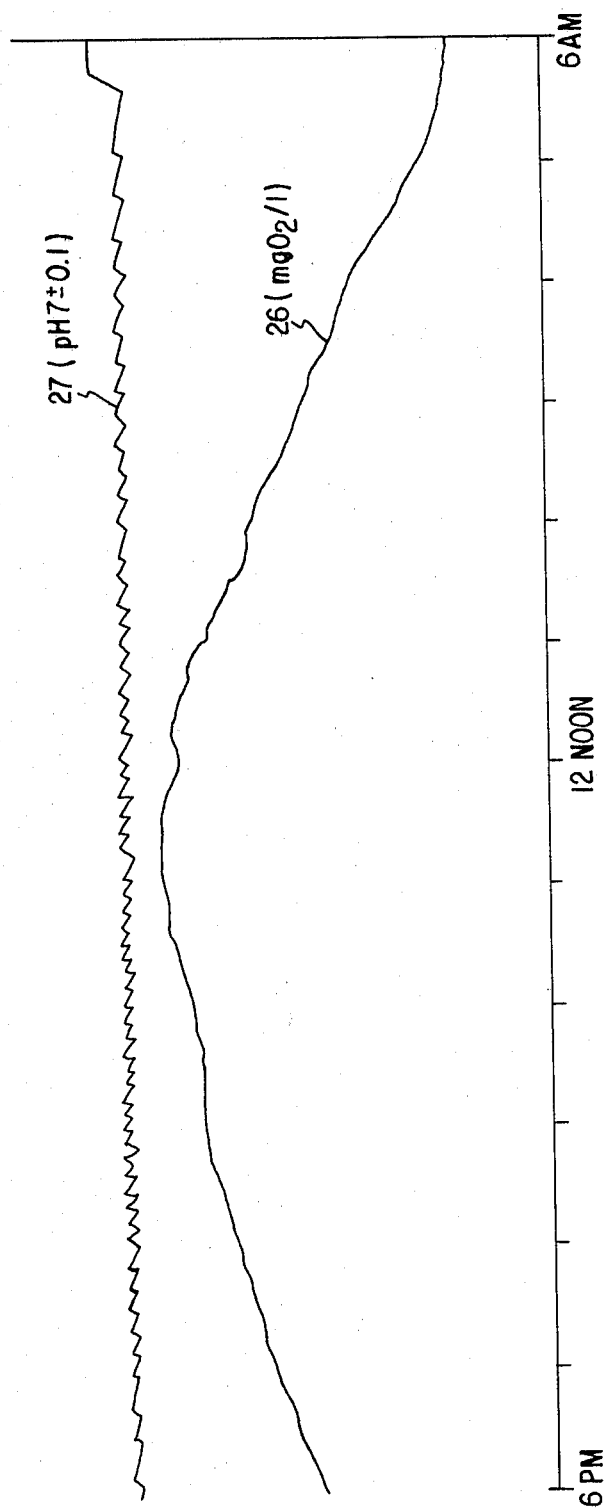

FIG. 7 is a diagram showing the measured values of the global radiation in calories per cm² and minutes plotted over time of day from 6:00 a.m. to 6:00 p.m. for the day of Sept. 4, 1975. FIG. 8 shows, in curve 26, for the same day the change in oxygen concentration in an algae suspension, measured in milligrams of oxygen per liter. The pH of the algae suspension fluctuates in dependence on the global radiation, and the pH is regulated to an almost constant value by the controlled introduction of $CO_2$ in accordance with the practice of the present invention. Curve 27 indicates the regulated pH of the algae suspension, and, as can be seen, the pH lies at 7 and fluctuates by about ± 0.1 pH.

Figure 9:
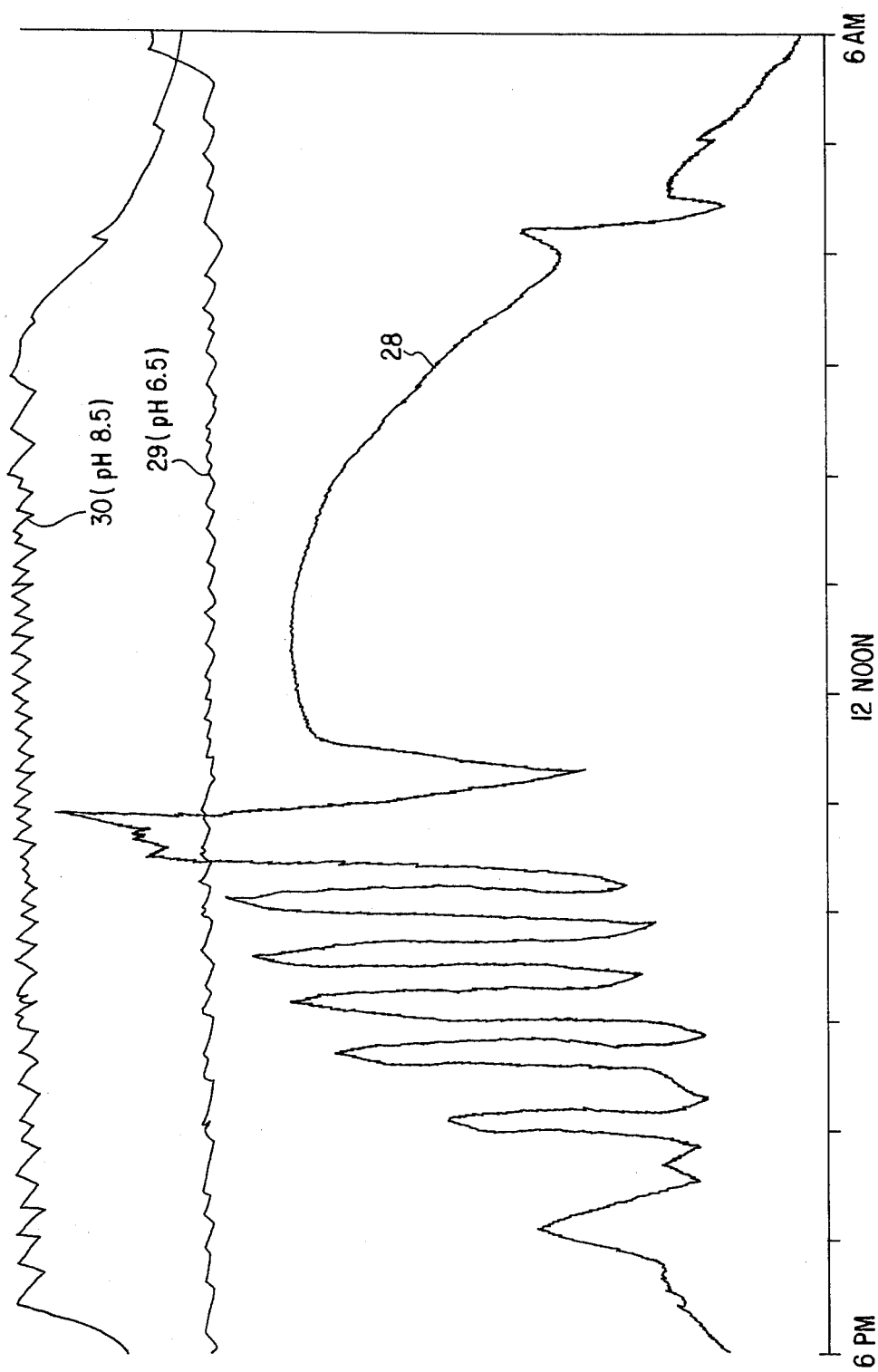

FIG. 9 shows the global radiation on Aug. 22, 1974 as curve 28. Two different algae suspensions are supplied with $CO_2$ on this day. The pH in each suspension fluctuates in dependence on this global radiation, and the pH in each suspension is regulated in accordance with the present invention by the controlled introduction of $CO_2$. Curve 29 shows the regulated pH of one of the suspensions which is regulated to a pH of 6.5 and curve 30 shows the regulated pH of the other suspension which is regulated to a pH of 8.5. It can be seen very clearly that the pH regulation itself reacts to major changes in global radiation during the day.

Figure 10:
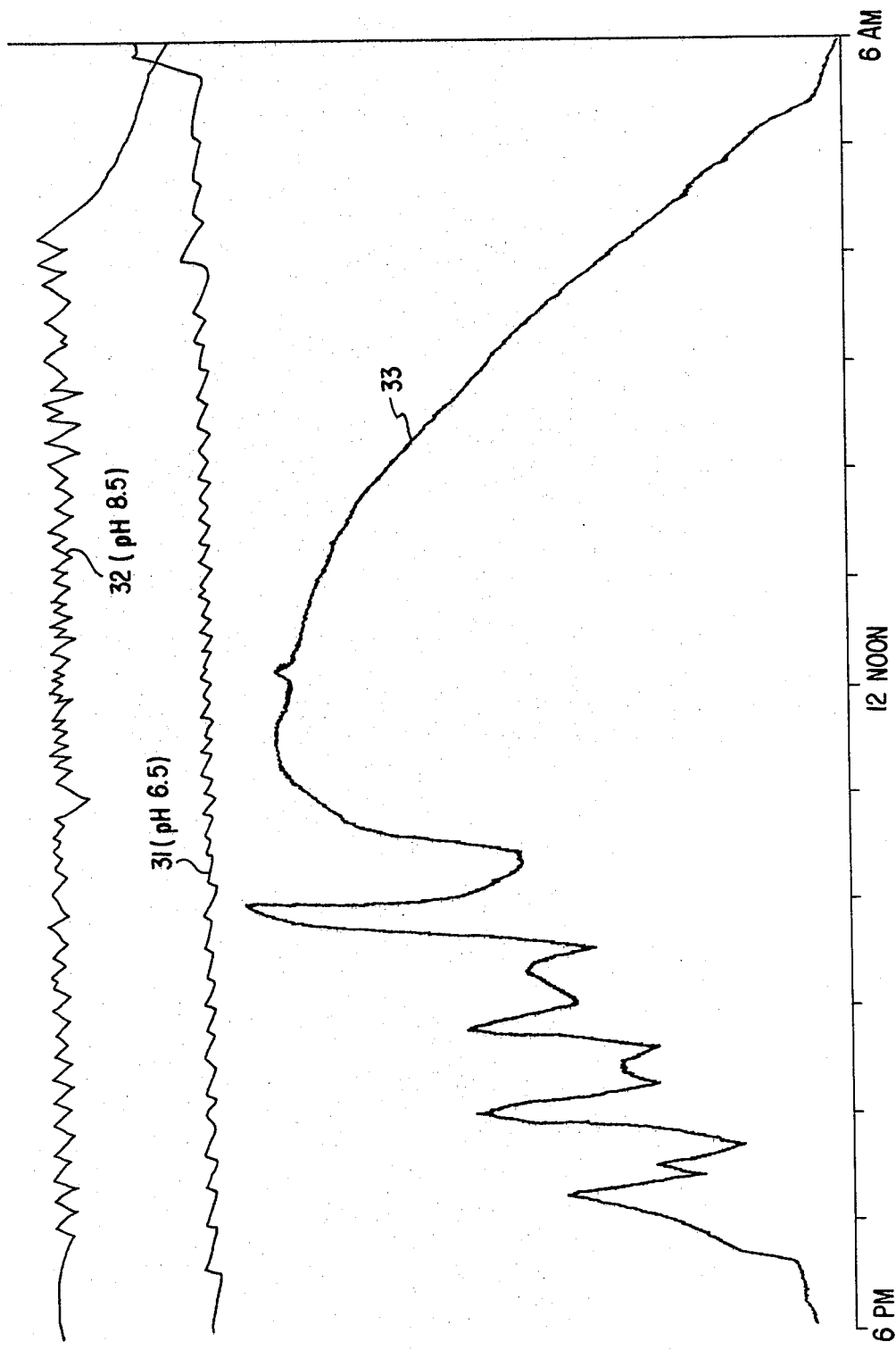

FIG. 10 shows the global radiation on Sept. 11, 1974 as curve 33. Two different algae suspensions are supplied with $CO_2$ on this day. The pH in each suspension fluctuates in dependence on the global radiation, and the pH in each suspension is regulated in accordance with the present invention by the controlled introduction of $CO_2$. Curve 31 shows the regulated pH of one of the suspensions which is regulated to a pH of 6.5 and curve 32 shows the regulated pH of the other suspension which is regulated to a pH of 8.5. As can be seen, the pH is regulated to an almost constant value in each suspension.

In principle all translucent plastic foils can be used, e.g. polyethylene foils of a thickness of 0.1 mm or more or plates from polymeric acrylic esters of a thickness of 1 mm or more. The height of the barrier layer is adjusted according to the hydromechanical conditions in the channel and the growth requirements of the cultivated organisms. This means that the barrier layer may be kept any where between the bottom of the channel and up to somewhat above the suspension surface.

The invention can also be applied in the mass production of autotrophic bacteria, photoheterotrophic bacteria, and aquatic angiosperms.

The pH values in FIGS. 8 to 10 are in the optimal range for Scenedesmus algae and *Coelastrum proboscideum*. The pH level to be maintained depends on the growth-rate dependence on $CO_2$ supply and on the cost of the $CO_2$ required. From these factors the most economic operational conditions can be calculated.

It will be understood that the above description of the present invention is susceptible to various modifications, changes and adaptations, and the same are intended to be comprehended within the meaning and range of equivalents of the appended claims.

What is claimed is:

1. Arrangement for optimally supplying autotrophic organisms with $CO_2$ nutrient comprising:
   (a) a culture channel in which a suspension of the organisms can be continuously moved in one direction, with the suspension being in open air and subjected to fluctuations of the intensity of the sun;
   (b) at least one discharge means in the channel for introducing $CO_2$ gas into the channel;
   (c) at least one control member connected to the discharge means for controlling the operation of the discharge means;
   (d) at least one pH measuring means in the channel for immersion into the suspension;
   (e) a circuit connecting the pH measuring means and the control member to actuate the control member for introducing the $CO_2$ in response to the pH measured by the pH measuring means; and
   (f) a light transmitting, but gas impermeable barrier layer in parallel with the direction of flow of the suspension above and downstream of the $CO_2$ discharge means to hold the $CO_2$ discharged into the channel below the barrier layer and thereby prevent the $CO_2$ from immediately rising to the surface of the suspension.

2. Arrangement as defined in claim 1 wherein the barrier layer is fastened below the surface of the suspension by a mount.

3. Arrangement as defined in claim 1 wherein the barrier layer is a foil.

4. Arrangement as defined in claim 1 including means for adjusting the height of the barrier layer with respect to the surface of the channel.

5. Arrangement as defined in claim 1 wherein the barrier layer is a plastic plate.

6. Arrangement as defined in claim 1 wherein the barrier layer is a glass plate.

* * * * *